United States Patent
Zhou et al.

(10) Patent No.: US 10,716,919 B2
(45) Date of Patent: Jul. 21, 2020

(54) EXPANDABLE SHEATH

(71) Applicant: Edwards Lifesciences Corporation, Irvine, CA (US)

(72) Inventors: Pu Zhou, Irvine, CA (US); Erik Bulman, Lake Forest, CA (US); Timothy A. Geiser, Laguna Niguel, CA (US); Michael G. Valdez, Riverside, CA (US); Yidong M. Zhu, Irvine, CA (US); Baigui Bian, Irvine, CA (US); Sonny Tran, Westminster, CA (US); Richard D. White, Poway, CA (US); Thanh Huy Le, Oceanside, CA (US); Tung T. Le, Irvine, CA (US); Alpana K. Gowdar, Newport Beach, CA (US); Yong Gao, Irvine, CA (US); David D. Williams, Bountiful, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/149,683

(22) Filed: Oct. 2, 2018

(65) Prior Publication Data
US 2019/0030298 A1 Jan. 31, 2019

Related U.S. Application Data

(63) Continuation of application No. 14/880,109, filed on Oct. 9, 2015, and a continuation of application No. 14/880,111, filed on Oct. 9, 2015.
(Continued)

(51) Int. Cl.
*A61M 25/06* (2006.01)
*A61F 2/24* (2006.01)
(Continued)

(52) U.S. Cl.
CPC ....... *A61M 25/0662* (2013.01); *A61F 2/2433* (2013.01); *A61F 2/958* (2013.01);
(Continued)

(58) Field of Classification Search
CPC .......... A61M 25/0662; A61M 25/0023; A61M 2025/0024; A61F 2/958; A61F 2/2433; A61F 2002/011
See application file for complete search history.

(56) References Cited

U.S. PATENT DOCUMENTS

| 4,601,713 A | 7/1986 | Fuqua |
| 4,710,181 A | 12/1987 | Fuqua |

(Continued)

FOREIGN PATENT DOCUMENTS

| EP | 0103546 | 3/1984 |
| EP | 0592410 | 10/1995 |

(Continued)

OTHER PUBLICATIONS

510K Premarket Notification, Jun. 22, 2018.
(Continued)

*Primary Examiner* — Christopher T Schatz
*Assistant Examiner* — Cynthia L Schaller
(74) *Attorney, Agent, or Firm* — Meunier Carlin & Curfman LLC; Joel B. German

(57) ABSTRACT

A delivery sheath includes an outer tubular layer and an initially folded inner tubular layer. When an implant passes therethrough, the outer tubular layer expands and the inner tubular layer unfolds into an expanded lumen diameter. The sheath may also include selectively placed longitudinal support rods that mediate friction between the inner and outer tubular layers to facilitate easy expansion, thereby reducing the push force needed to advance the implant through the sheath's lumen.

18 Claims, 15 Drawing Sheets

Related U.S. Application Data

(60) Provisional application No. 62/145,968, filed on Apr. 10, 2015.

(51) Int. Cl.
*A61F 2/958* (2013.01)
*A61F 2/01* (2006.01)
*A61M 25/00* (2006.01)

(52) U.S. Cl.
CPC .... *A61F 2002/011* (2013.01); *A61M 25/0023* (2013.01); *A61M 2025/0024* (2013.01)

(56) References Cited

U.S. PATENT DOCUMENTS

| | | | |
|---|---|---|---|
| 4,738,666 A | 4/1988 | Fuqua et al. |
| 4,921,479 A | 5/1990 | Grayzel |
| 5,104,388 A | 4/1992 | Quackenbush |
| 5,318,588 A | 6/1994 | Horzewski et al. |
| 5,320,611 A | 6/1994 | Bonutti et al. |
| 5,501,667 A | 3/1996 | Verduin, Jr. |
| 5,674,240 A | 10/1997 | Bonutti et al. |
| 5,810,776 A | 9/1998 | Bacich et al. |
| 5,817,100 A | 10/1998 | Igaki |
| 5,997,508 A | 12/1999 | Lunn et al. |
| 6,080,141 A | 6/2000 | Castro et al. |
| 6,090,072 A | 7/2000 | Kratoska et al. |
| 6,090,136 A | 7/2000 | McDonald et al. |
| 6,190,357 B1 | 2/2001 | Ferrari et al. |
| 6,312,443 B1 | 11/2001 | Stone |
| 6,346,092 B1 | 2/2002 | Leschinsky |
| 6,358,238 B1 | 3/2002 | Sherry |
| 6,443,979 B1 | 9/2002 | Stalker et al. |
| 6,494,860 B2 | 12/2002 | Rocamora et al. |
| 6,632,236 B2 | 10/2003 | Hogendijk |
| 6,652,492 B1 | 11/2003 | Bell et al. |
| 6,702,830 B1 | 3/2004 | Demarais et al. |
| 6,814,715 B2 | 11/2004 | Bonutti et al. |
| 6,899,727 B2 | 5/2005 | Armstrong et al. |
| 7,438,712 B2 | 10/2008 | Chouinard |
| 7,591,832 B2 | 9/2009 | Eversull et al. |
| 7,655,016 B2 | 2/2010 | Demarais et al. |
| 7,665,016 B2 | 2/2010 | Behrens et al. |
| 7,678,128 B2 | 3/2010 | Boyle et al. |
| 7,699,864 B2 | 4/2010 | Kick et al. |
| 7,713,193 B2 | 5/2010 | Nance et al. |
| 7,722,568 B2 | 5/2010 | Lenker et al. |
| 7,762,995 B2 | 7/2010 | Eversull et al. |
| 7,766,820 B2 | 8/2010 | Core |
| 7,780,692 B2 | 8/2010 | Nance et al. |
| 7,785,360 B2 | 8/2010 | Freitag |
| 7,837,692 B2 | 11/2010 | Mulholland et al. |
| 7,892,203 B2 | 2/2011 | Lenker et al. |
| 7,927,309 B2 | 4/2011 | Palm |
| 7,951,110 B2 | 5/2011 | Bishop et al. |
| 7,963,952 B2 | 6/2011 | Wright, Jr. et al. |
| 8,034,072 B2 | 10/2011 | Van Nguyen et al. |
| 8,048,034 B2 | 11/2011 | Eversull et al. |
| 8,090,936 B2 | 1/2012 | Fallon et al. |
| 8,092,481 B2 | 1/2012 | Nance et al. |
| 8,252,015 B2 | 8/2012 | Leeflang et al. |
| 8,282,664 B2 | 10/2012 | Nance et al. |
| 8,337,518 B2 | 12/2012 | Nance et al. |
| 8,414,645 B2 | 4/2013 | Dwork et al. |
| 8,562,559 B2 | 10/2013 | Bishop et al. |
| 8,562,673 B2 | 10/2013 | Yeung et al. |
| 8,597,277 B2 | 12/2013 | Lenker et al. |
| 8,652,203 B2 | 2/2014 | Quadri et al. |
| 8,668,668 B2 | 3/2014 | Bishop et al. |
| 8,690,936 B2 | 4/2014 | Nguyen et al. |
| 8,728,153 B2 | 5/2014 | Bishop et al. |
| 8,790,387 B2 | 7/2014 | Nguyen et al. |
| 8,852,257 B2 * | 10/2014 | Liu .................. A61F 2/958 623/1.11 |
| 8,900,191 B2 | 12/2014 | Lenker et al. |
| 8,900,214 B2 | 12/2014 | Nance et al. |
| 9,044,577 B2 | 6/2015 | Bishop et al. |
| 9,192,751 B2 | 11/2015 | MacAulay et al. |
| 9,192,752 B2 | 11/2015 | Leeflang et al. |
| 9,241,735 B2 | 1/2016 | Kick et al. |
| 9,254,374 B2 | 2/2016 | Thorstenson et al. |
| 9,259,813 B2 | 2/2016 | Heideman et al. |
| 9,301,840 B2 | 4/2016 | Nguyen et al. |
| 9,301,841 B2 | 4/2016 | Nguyen et al. |
| 9,320,508 B2 | 4/2016 | Carroux |
| 9,387,314 B2 | 7/2016 | Bishop et al. |
| 9,393,041 B2 | 7/2016 | Barker et al. |
| 9,440,054 B2 | 9/2016 | Bishop et al. |
| 9,642,704 B2 | 5/2017 | Tuval et al. |
| 9,788,944 B2 | 10/2017 | Daly et al. |
| 9,801,619 B2 | 10/2017 | Lenker et al. |
| 9,907,931 B2 | 3/2018 | Birmingham et al. |
| 2002/0032459 A1 | 3/2002 | Horzewski et al. |
| 2002/0123793 A1 | 9/2002 | Schaldach et al. |
| 2003/0004537 A1 | 1/2003 | Boyle et al. |
| 2004/0087968 A1 | 5/2004 | Core et al. |
| 2004/0122415 A1 | 6/2004 | Johnson |
| 2005/0080430 A1 | 4/2005 | Wright et al. |
| 2005/0085842 A1 | 4/2005 | Eversull et al. |
| 2005/0125021 A1 | 6/2005 | Nance et al. |
| 2006/0020321 A1 | 1/2006 | Parker |
| 2006/0135962 A1 | 6/2006 | Kick et al. |
| 2006/0135981 A1 | 6/2006 | Lenker et al. |
| 2006/0217755 A1 | 9/2006 | Eversull et al. |
| 2007/0021768 A1 | 1/2007 | Nance et al. |
| 2007/0074805 A1 | 4/2007 | Leeflang et al. |
| 2007/0087148 A1 | 4/2007 | Okushi et al. |
| 2008/0004521 A1 | 1/2008 | Hundley et al. |
| 2008/0004571 A1 | 1/2008 | Voss |
| 2008/0114331 A1 | 5/2008 | Holman et al. |
| 2008/0243081 A1 | 10/2008 | Nance et al. |
| 2010/0094209 A1 | 4/2010 | Drasler et al. |
| 2010/0094392 A1 | 4/2010 | Nguyen et al. |
| 2010/0198160 A1 | 8/2010 | Voss |
| 2011/0112567 A1 | 5/2011 | Lenker et al. |
| 2011/0190697 A1 | 8/2011 | Farnan |
| 2011/0251681 A1 | 10/2011 | Shipley et al. |
| 2012/0116439 A1 | 5/2012 | Ho |
| 2012/0158033 A1 | 6/2012 | Deal et al. |
| 2012/0323180 A1 | 12/2012 | Chebator et al. |
| 2013/0030369 A1 | 1/2013 | Root et al. |
| 2013/0281787 A1 | 3/2013 | Avneri et al. |
| 2013/0131718 A1 | 5/2013 | Jenson et al. |
| 2013/0178711 A1 | 7/2013 | Avneri et al. |
| 2013/0231735 A1 | 9/2013 | Deem et al. |
| 2014/0121629 A1 | 5/2014 | MacAulay et al. |
| 2014/0236122 A1 | 8/2014 | Anderson et al. |
| 2014/0236123 A1 | 8/2014 | Birmingham et al. |
| 2014/0379067 A1 | 12/2014 | Nguyen et al. |
| 2015/0182723 A1 | 7/2015 | Leeflang et al. |
| 2015/0238178 A1 | 8/2015 | Carroux |
| 2015/0265798 A1 | 9/2015 | Nihonmatsu et al. |
| 2015/0320971 A1 | 11/2015 | Leeflang et al. |
| 2016/0074067 A1 | 3/2016 | Furnish et al. |
| 2016/0135840 A1 | 5/2016 | Kick et al. |
| 2016/0213882 A1 | 7/2016 | Fitterer et al. |
| 2016/0296332 A1 | 10/2016 | Zhou et al. |
| 2016/0296730 A1 | 10/2016 | Zhou et al. |
| 2017/0014157 A1 | 1/2017 | Coyle et al. |
| 2017/0072163 A1 | 3/2017 | Lim et al. |
| 2017/0209133 A1 | 7/2017 | Ciulla et al. |
| 2017/0245864 A1 | 8/2017 | Franano et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0229000 A1 | 8/2018 | Anderson et al. |
| 2018/0326186 A1 | 11/2018 | Zhou et al. |

FOREIGN PATENT DOCUMENTS

| | | |
|---|---|---|
| EP | 1139889 | 4/2006 |
| EP | 1804860 | 4/2014 |
| EP | 2288403 | 11/2014 |
| EP | 2862590 | 4/2015 |

(56) References Cited

FOREIGN PATENT DOCUMENTS

| | | |
|---|---|---|
| EP | 1694398 | 3/2016 |
| EP | 2101661 | 3/2016 |
| EP | 2995268 | 3/2016 |
| EP | 2475417 | 10/2018 |
| JP | 2012040145 | 3/2012 |
| WO | 2004037333 | 5/2004 |
| WO | 2008147964 | 12/2008 |
| WO | 2009035745 | 3/2009 |
| WO | 2013044942 | 4/2013 |
| WO | 2014140093 | 9/2014 |
| WO | 2018148488 | 8/2018 |

OTHER PUBLICATIONS

BSX Structural Heart Update 2018, Feb. 2018.
Related U.S. Appl. No. 14/880,111 and the file history thereof.
Related U.S. Appl. No. 16/149,947 and the file history thereof.
Related U.S. Appl. No. 16/036,190 and the file history thereof.
Related U.S. Appl. No. 14/324,894 and the file history thereof.
Related U.S. Appl. No. 14/312,739 and the file history thereof.
Related U.S. Appl. No. 12/249,867 and the file history thereof.
Related U.S. Appl. No. 15/057,953 and the file history thereof.
Related U.S. Appl. No. 16/149,969 and the file history thereof.
Related U.S. Appl. No. 16/149,953 and the file history thereof.
Related U.S. Appl. No. 16/149,956 and the file history thereof.
Related U.S. Appl. No. 16/149,960 and the file history thereof.
Related U.S. Appl. No. 14/880,109 and the file history thereof.
Related U.S. Appl. No. 16/149,636 and the file history thereof.
Related U.S. Appl. No. 16/149,650 and the file history thereof.
Related U.S. Appl. No. 16/149,671 and the file history thereof.
Related U.S. Appl. No. 16/149,697 and the file history thereof.

* cited by examiner

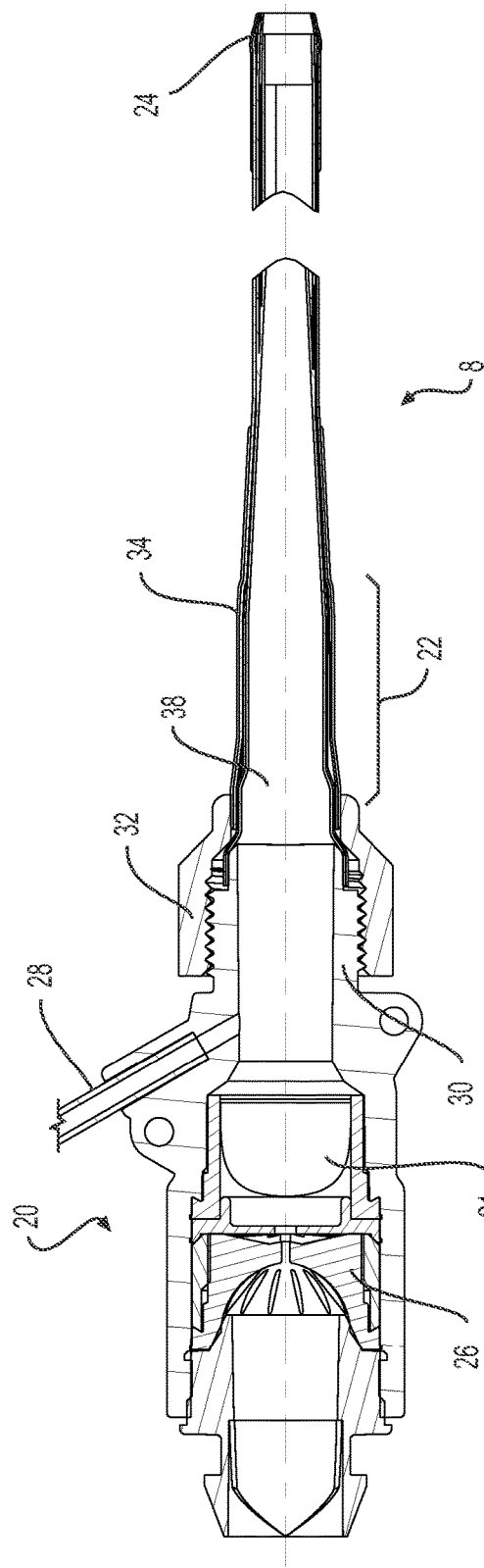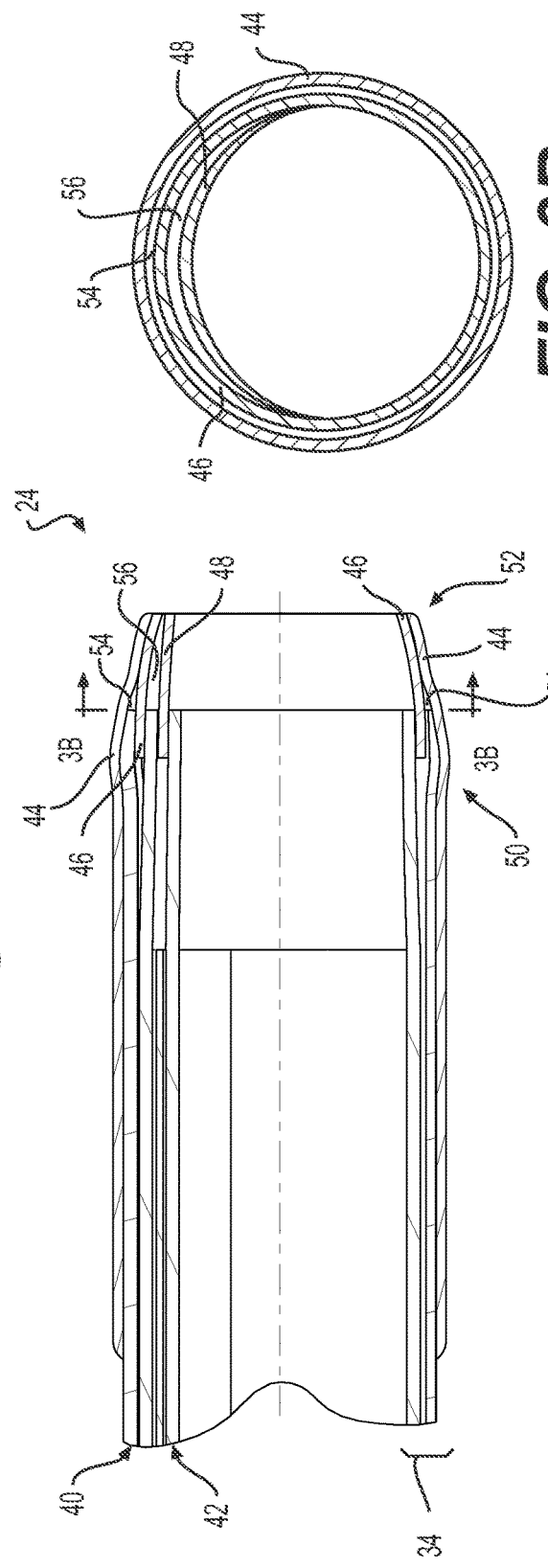

EXPANDABLE SHEATH

RELATED APPLICATIONS

This application is a continuation of U.S. application Ser. No. 14/880,109, filed Oct. 9, 2015 and entitled EXPANDABLE SHEATH, which claims the benefit of U.S. Provisional Patent Application Ser. No. 62/145,968 filed on Apr. 10, 2015 and entitled EXPANDABLE DELIVERY SHEATH. This application is also a continuation of U.S. application Ser. No. 14/880,111, filed Oct. 9, 2015 and entitled EXPANDABLE SHEATH WITH ELASTOMERIC CROSS SECTIONAL PORTIONS, which claims the benefit of U.S. Provisional Patent Application Ser. No. 62/145,968, filed Apr. 10, 2015 and entitled EXPANDABLE DELIVERY SHEATH. All of the aforementioned applications are hereby incorporated by reference herein in their entireties and for all purposes.

FIELD

The present application concerns embodiments of a sheath for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

U.S. Pat. No. 8,790,387, which is entitled EXPANDABLE SHEATH FOR INTRODUCING AN ENDOVASCULAR DELIVERY DEVICE INTO A BODY and is incorporated herein by reference, discloses a sheath with a split outer polymeric tubular layer and an inner polymeric layer, for example in FIGS. 27A and 28. A portion of the inner polymeric layer extends through a gap created by the cut and can be compressed between the portions of the outer polymeric tubular layer. Upon expansion of the sheath, portions of the outer polymeric tubular layer have separated from one another, and the inner polymeric layer is expanded to a substantially cylindrical tube. Advantageously, the sheath disclosed in the '387 patent can temporarily expand for passage of implantable devices and then return to its starting diameter.

Despite the disclosure of the '387 patent, there remains a need for further improvements in introducer sheaths for endovascular systems used for implanting valves and other prosthetic devices.

SUMMARY

The needs above and other advantages are provided by an expandable introducer sheath for a delivery of an implant mounted on a catheter. The sheath includes an elastic outer tubular layer and an inner tubular layer having a thick wall portion integrally connected to a thin wall portion. The inner tubular layer can have a compressed condition/folded configuration wherein the thin wall portion folds onto an outer surface of the thick wall portion under urging of the elastic outer tubular layer. When the implant passes therethrough, the outer tubular layer stretches and the inner tubular layer at least partially unfolds into an expanded lumen diameter to accommodate the diameter of the implant. Once the implant passes, the outer tubular layer again urges the inner tubular layer into the folded configuration with the sheath reassuming its smaller profile. In addition to a reduced initial profile size, the integral construction of the inner tubular layer guards against the leaks and snags of prior art split-tube and uniform thickness liner combinations. The sheath may also include selectively placed longitudinal rods that mediate friction between the inner and outer tubular layers to facilitate easy expansion and collapse, thereby reducing the push force needed to advance the oversized implant through the sheath's lumen.

Embodiments include a sheath for delivery of an implant mounted on a catheter. The sheath may include an elastic outer tubular layer and an inner tubular layer. The outer tubular layer defines an initial elastic lumen extending axially therethrough and having an initial diameter. The inner tubular layer has a thick wall portion integrally connected to a thin wall portion—such as by co-extrusion during manufacture. The thick wall portion has a C-shaped cross section with a first longitudinally extending end and a second longitudinally extending end. The thin wall portion extends between the first and second longitudinally extending ends to define an expanded lumen extending axially through the inner tubular layer. The expanded lumen has an expanded diameter larger than the initial diameter of the initial elastic lumen. The inner tubular layer, in a compressed condition, extends through the initial elastic lumen of the elastic outer tubular layer with the elastic outer tubular layer urging the first longitudinally extending end under the second longitudinally extending end of the inner tubular layer. The inner tubular layer in a locally expanded condition has the first and second longitudinally extending ends radially expanded apart, against the urging of the elastic outer tubular layer by passage of the implant, into a non-overlapping condition with the thin wall portion extending therebetween to form the expanded lumen. The inner tubular layer is configured to be urged by the outer elastic tubular layer into the compressed condition after passage of the implant through the expanded lumen.

In another aspect, the outer surface of the inner tubular layer and/or the inner surface of the outer tubular layer can have a lubricious coating configured to allow free relative sliding of the outer elastic layer and inner tubular layer. A longitudinally extending portion or strip of the outer surface of the inner tubular layer can be adhered to a corresponding longitudinally extending portion of the inner surface of the outer tubular layer to provide some restriction on rotation between the inner and outer layer.

In another embodiment, the tubular layers may include a plurality of longitudinal rods coupled to their surfaces. For example, the inner surface of the outer tubular layer may include rods extending into the initial elastic lumen. The rods are configured to provide a bearing surface to facilitate relative movement of the layers when moving from the locally expanded condition to the compressed condition (and back). Longitudinal rods embedded within the elastic outer tubular layer can also protrude from both an inner and outer surface of the elastic outer tubular layer.

The longitudinal rods may be circumferentially spaced about the inner surface of the outer tubular layer. The inner tubular layer may also include contact-area reducing rods coupled to its inner surface.

In another aspect, the sheath can include a radiopaque tubular layer extending around a longitudinal portion of the elastic outer tubular layer. In some embodiments, the outer tubular layer is comprised of a transparent material In some embodiments, a heat-shrink tube can be applied around the elastic outer tubular layer at a distal end of the elastic outer tubular layer.

In some embodiments, a distal portion of the elastic outer tubular layer and inner tubular layer are adhered to each other. For example, a distal portion of the elastic outer tubular layer can be adhered to an expanded outer surface of the inner tubular layer. The distal portion of the elastic outer tubular layer and inner tubular layer can be reflowed onto each other into a sealed configuration. In some implementations, a distal portion of the sheath has a flared shape. The flared shape can be folded into an overlapping arrangement.

A method of using the expandable introducer sheath can include inserting the sheath, at least partially, into the blood vessel of the patient. An implant is advanced through the inner tubular layer of the sheath. The inner tubular layer transitions from a compressed condition to a locally expanded condition using the outwardly directed radial force of the implant. After passage of the implant, the locally expanded inner tubular layer is contracted at least partially back to the compressed condition by the inwardly directed radial force of the outer elastic tubular layer. During the local expansion of the inner tubular layer, the first and second longitudinally extending ends move towards and then away from each other. During contraction of the locally expanded inner tubular layer, the first and second longitudinally extending ends move toward and then away from each other to return, at least partially, to the compressed condition.

DESCRIPTION OF DRAWINGS

FIG. 2 is a cross sectional view of a sheath and a hub.

FIG. 3A is a magnified view of distal tip of the sheath.

FIG. 3B is a cross sectional view of the distal tip of the sheath, taken along line 3B-3B of FIG. 3A.

DETAILED DESCRIPTION

Figure 1:
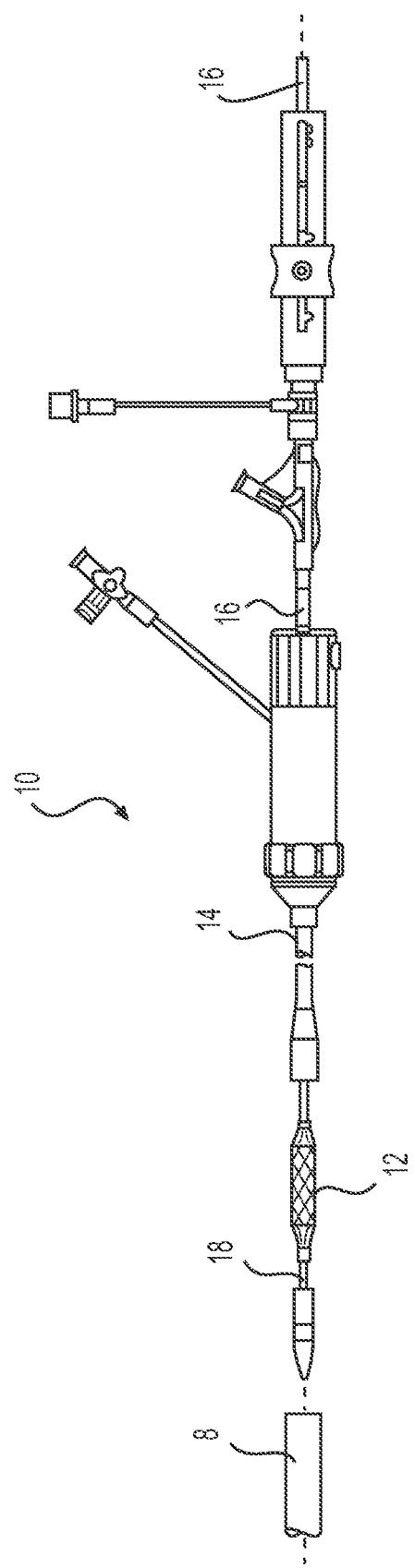
FIG. 1 is an elevation view of an expandable sheath along with an endovascular delivery apparatus for implanting a prosthetic implant.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed embodiments of an expandable sheath can minimize trauma to the vessel by allowing for temporary expansion of a portion of the introducer sheath to accommodate the delivery system, followed by a return to the original diameter once the device passes through. The expandable sheath can include, for example, an integrally formed inner tubular layer with thick and thin wall portions, wherein the thin wall portion can expand to an expanded lumen for passage of an implant and then fold back onto itself under biasing of an outer elastic tubular layer after departure of the implant. In another aspect, the expandable sheath can include one or more longitudinally oriented stiffening elements (such as rods) that are coupled to the elastic outer layer to provide stiffness for the expandable sheath. Some embodiments can comprise a sheath with a smaller profile than the profiles of prior art introducer sheaths. Furthermore, present embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can avoid the need for multiple insertions for the dilation of the vessel.

Disclosed herein are elongate delivery sheaths that are particularly suitable for delivery of implants in the form of implantable heart valves, such as balloon-expandable implantable heart valves. Balloon-expandable implantable heart valves are well-known and will not be described in detail here. An example of such an implantable heart valve is described in U.S. Pat. No. 5,411,552, and also in U.S. Patent Application Publication No. 2012/0123529, both of which are hereby incorporated by reference. The elongate delivery sheaths disclosed herein may also be used to deliver other types of implantable devices, such as self-expanding implantable heart valves, stents or filters. The term "implantable" as used herein is broadly defined to mean anything—prosthetic or not—that is delivered to a site within a body. A diagnostic device, for example, may be an implantable.

FIG. 1 illustrates an exemplary sheath 8 in use with a representative delivery apparatus 10, for delivering an implant 12, or other type of implantable, to a patient. The apparatus 10 can include a steerable guide catheter 14 (also referred to as a flex catheter) and a balloon catheter 16 extending through the guide catheter 14. The guide catheter 14 and the balloon catheter 16 in the illustrated embodiment are adapted to slide longitudinally relative to each other to facilitate delivery and positioning of the implant 12 at an implantation site in a patient's body, as described in detail below. The sheath 8 is an elongate, expandable tube that can include a hemostasis valve at the opposite, proximal end of the sheath to stop blood leakage.

Generally, during use a distal end of the sheath 8 is passed through the skin of the patient and inserted into a vessel, such as the trans-femoral vessel. The delivery apparatus 10 can be inserted into the sheath 8 through the hemostasis valve, and the implant 12 can then be delivered and implanted within the patient.

As shown in FIG. 2, the sheath 8 includes a hub 20, a flared proximal end 22 and a distal tip 24. The hub 20 is constructed of a rigid cylindrical structure defining a hub lumen 21 and houses a hemostasis valve 26 and may define a side port 28 and have a threaded distal end 30. The flared proximal end 22 of the sheath 8 includes a threaded female connector 32 mounted on a tubular wall structure 34. The distal tip 24 of the sheath 8 is mounted over a distal end of the tubular wall structure 34, as shown in FIG. 3. The tubular wall structure 34 defines a central lumen 38.

The hub 20 is attached to the flared proximal end 22 by twisting the threaded distal male end 30 into correspondingly threaded female connector 32. This places the hub lumen 21 in communication with the central lumen 38 of the tubular wall structure 34. The hemostasis valve 26 mediates access by the delivery apparatus 10 to the hub lumen 21 and central lumen 38 and ultimate deployment of the implant 12 in a pressurized (blood filled) environment. Side port 28 provides an additional access for application of saline or other fluids.

The distal tip 24, meanwhile, provides some restraint to the otherwise radially expandable tubular wall structure 34. The distal tip 24 also helps with advancement over an introducer by providing a tapered advancement surface. Further the distal tip 24 improves the stiffness of the sheath 8 at its distal tip to guard against buckling or collapse of the tubular wall structure 34 during torque and advancement forces.

As shown in FIG. 3A, the tubular wall structure 34 includes an elastic outer tubular layer 40 and an inner tubular layer 42 and the distal tip 24. The distal tip 24 generally has a tubular structure with a slightly tapering or frusto-conical distal end. The distal tip 24 includes an outer wall 44, an inner wall 46 and a retainer 48. The outer wall 44 has an axial length longer than the inner wall 46. A proximal end of the outer wall 44 has a tubular shape with straight sides. The outer wall tapers to a neck 52 at its distal free end and begins to flare slightly to a cylindrical bulge 50 moving proximally from the distal free end. The neck 52 has a smaller diameter than the proximal tubular end of the outer wall 44. The proximal tubular end in turn has a smaller diameter than the cylindrical bulge 50.

The inner wall 46 has a shorter axial length than the outer wall but also has a cylindrical shape that tapers—although more gradually—toward its distal free end. An outer surface of the inner wall 46 and inner surface of the outer wall 44 define an annular space 54 which is configured to receive a distal free end of the elastic outer tubular layer 40, as shown in FIG. 3A. The annular space 54 bulges some due to its position subjacent the cylindrical bulge 50 of the outer wall 44. This bulge facilitates insertion and capture of the elastic outer tubular layer. The annular space 54 tapers to a point moving distally as the surfaces of the outer wall 44 and inner wall 46 converge into binding contact.

The retainer 48 is an additional arc-shaped wall that extends along a portion of the inner surface of the inner wall 46 and defines its own crescent-shaped space 56, as shown in the cross section of FIG. 3B. The crescent-shaped space 56 is configured to receive a foldable thin wall portion of the inner tubular layer 42, as will be described in more detail below. The retainer 48 has an arc size that corresponds with a circumferential arc-length of the folded over portion of the inner tubular layer 42 when it is in its compressed or folded configuration. Advantageously, the distal tip 24 helps to increase the structural rigidity of the distal end of the tubular wall structure 34, blocks blood flow between the layers and provides a smooth, tapered profile for pushing through tissue when advanced over a wire or dilator.

Figure 4:
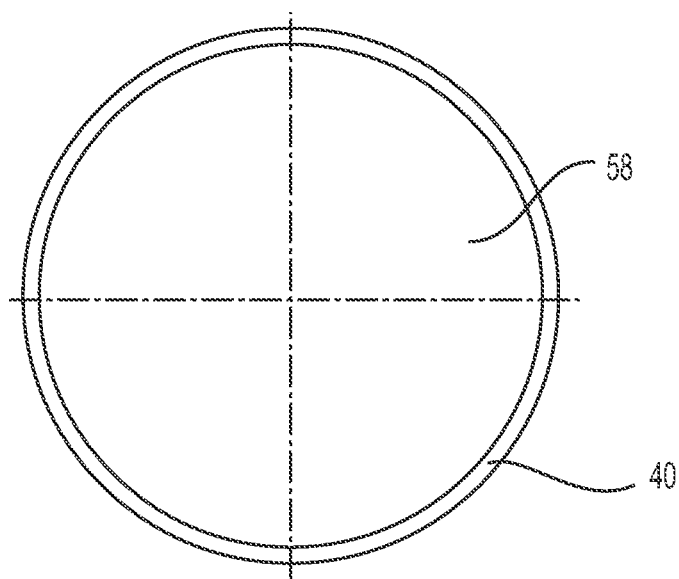
FIG. 4 is a cross sectional view of an exemplary implementation of the outer tubular layer of the sheath.

As shown in FIG. 4, the outer tubular layer 40 of one embodiment has a cylindrical shape with a circular cross-section along its entire length. The outer tubular layer 40 defines an initial elastic lumen 58 extending axially through its cylindrical cross-section. The outer tubular layer is sized to accommodate the delivery passage of the patient and/or the size of the implant 12 to be delivered. For example, the inside diameter, ID, of the layer 40 may be 0.185 inches and may have a wall thickness of 0.005+/−0.001 inches for delivery of a stent-mounted heart valve through trans-femoral access. In one aspect, inner surface of the outer tubular layer 40 and/or outer surface of the inner tubular layer 42 may be treated to have or have applied thereto a lubricious coating to facilitate unfolding and folding of the inner tubular layer 42.

The elastic lumen 58 is referred to as "initial" to designate its passive or as-formed diameter or cross-sectional dimension when not under the influence of outside forces, such as the implant 12 passing therethrough. It should be noted, however, that because the outer tubular layer 40 is comprised in the illustrated embodiment by an elastic material it may not retain its shape under even light forces such as gravity. Also, the outer tubular layer 40 need not have a cylindrical cross-section and instead could have oval, square or other cross-sections which generally can be configured to meet the requirements of the inner tubular layer 42 and/or expected shape of the implant 12. Thus, the term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

The outer tubular layer 40, in one implementation, is constructed of a relatively elastic material that has enough flexibility to mediate the expansion induced by passage of the implant 12 and expansion of the inner tubular layer 42 while at the same time having enough material stiffness to urge the inner tubular layer back into an approximation of the initial diameter once the implant has passed. An exemplary material includes NEUSOFT. NEUSOFT is a translucent polyether urethane based material with good elasticity, vibration dampening, abrasion and tear resistance. The polyurethanes are chemically resistant to hydrolysis and suitable for overmolding on polyolefins, ABS, PC, Pebax and nylon. The polyuerthane provides a good moisture and oxygen barrier as well as UV stability. One advantage of the outer tubular layer 40 is that it provides a fluid barrier for the pressurized blood. Other materials having similar properties of elasticity may also be used for the elastic outer tubular layer 40.

Figure 5:
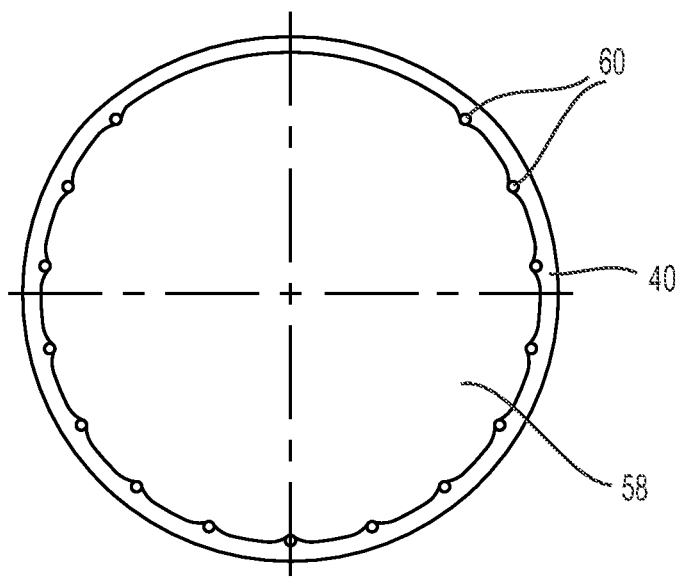
FIG. 5 is a cross sectional view of another exemplary implementation of the outer tubular layer of the sheath.
Figure 6:
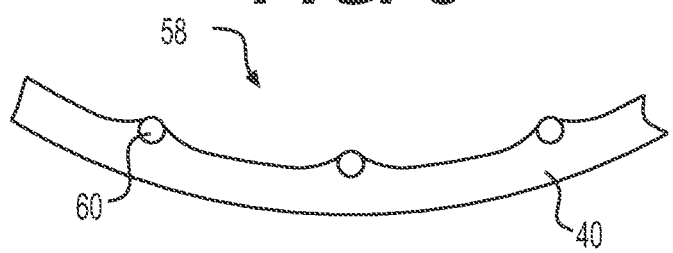
FIG. 6 is a magnified view of part of the outer tubular layer of FIG. 5, showing the cross section of longitudinal rods in greater detail.

FIG. 5 shows another implementation of the elastic outer tubular layer 40 including a plurality of longitudinal rods 60. The longitudinal rods 60 extend the length of the outer tubular layer 40 and protrude into the initial elastic lumen 58. The longitudinal rods 60 are coupled to the outer tubular layer, such as by being co-extruded and/or embedded into the elastic material of the outer tubular layer, as shown in FIG. 6. Advantageously, the longitudinal rods 60 are configured to provide a bearing surface to facilitate relative movement of the inner tubular layer 42 within the outer tubular layer 40. This is especially helpful when the inner tubular layer 42 is unfolding and returning to its originally folded shape.

The longitudinal rods 60 may be circumferentially spaced about the inside surface of the outer tubular layer 60. Although fifteen longitudinal rods 60 are shown in the cross-section of FIG. 5, any number, including a single one, of longitudinal rods may be employed. Also, the longitudinal rods 60 need not extend the entire length of the outer tubular layer 60. They may instead be applied selectively depending upon the demands of the implant, application and other circumstances. Longitudinal rods 60 may be selectively left out of an overall spacing pattern, such as in FIG. 5 where approximately 90 degrees of the inside surface of the outer tubular layer 40 is left as an unadorned surface.

As shown in FIG. 6, the longitudinal rods may have a circular cross-section so as to present a curved bearing surface into the elastic lumen 58. Although diameters for the longitudinal rods 60 may vary, in one embodiment they are 0.004 inches in diameter. The outermost part of the longitudinal rod is positioned about 0.006 inches from the outside surface of the outer tubular layer 40. In this manner, the inner edge surface of the longitudinal rods 60 spaces the inner tubular layer 42 from the surface of the outer tubular layer 40, thus reducing friction or the tendency to stick and impede relative movement. In other embodiments, the longitudinal rods can have other shapes, and the shapes may change within a single rod along the longitudinal direction. As also shown in FIG. 6, the material of the outer tubular layer 40 extends up in a slope past the midpoint of the cross-section of the longitudinal rods 60 for extra stability.

Figure 7:
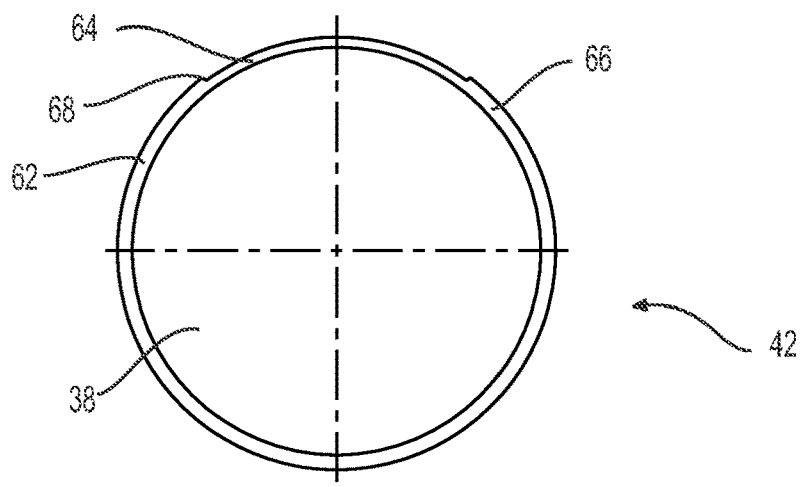
FIG. 7 is a cross section of an exemplary implementation of the inner tubular layer of the sheath.

As shown in FIG. 7, the inner tubular layer 42 has a thick wall portion 62 integrally extruded with a thin wall portion 64. The thick wall portion 62 is approximately 0.011+/−0.001 inches and the thin wall portion 66 is approximately 0.0065+/−0.0010 inches. The inner tubular layer 42 is preferably constructed of a relatively (compared to the outer tubular layer 40) stiff material such as a stiff polymer like high density polyethylene (HDPE) or an equivalent polymer. Integral construction, such as integral extrusion, of the wall portions advantageously avoids the leakage of prior-art sheaths that use a split in the sheath to promote expandability. Prior-art C-sheaths tend to leak close to the proximal end at the manifold where the sheath is stretched the most. Also, integral construction improves the ability to torque the sheath 8.

The thick wall portion 62, in the illustrated embodiment of FIG. 7, has a C-shaped cross section with a first longitudinally extending end 66 and a second longitudinally extending end 68. The ends are where the thickness of the thick wall portion 62 starts to narrow to thin portion 64 on the cross-section. That transition extends longitudinally in the direction of the axis of the sheath 8, such that the thick wall portion 62 forms an elongate C-shaped channel.

From those ends 66, 68 of the thick wall portion 62 extends the thin wall portion 64 and together they define a tubular shape. Extending longitudinally in that tubular shape is the central lumen 38. FIG. 7, in particular, shows the central lumen 38 in its expanded diameter which is larger than the initial diameter of the elastic outer tubular layer 40. For example, the inner tubular layer 42 has a central lumen 38 that is about 0.300+/−0.004 inches. The outer tubular layer 40 has an initial elastic lumen 58 of about 0.185 inches.

Figure 8:
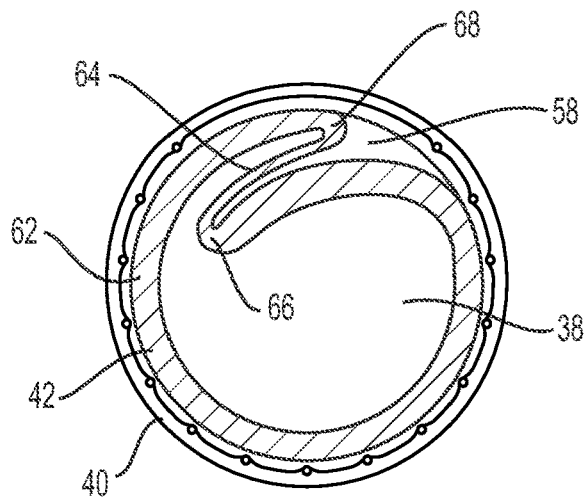
FIG. 8 is a cross section of both the inner and outer tubular layers of the sheath. In this example, the inner tubular layer is in the compressed condition.
Figure 9:
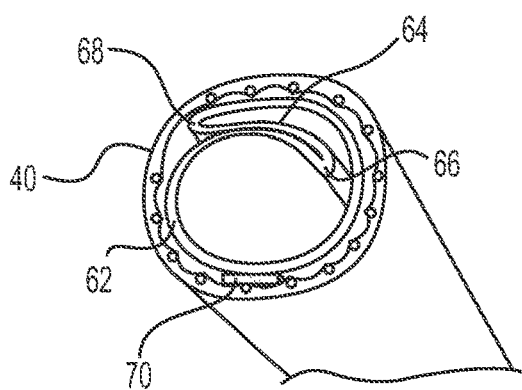
FIG. 9 is a perspective view of the distal end of an implementation of the expandable sheath.

FIGS. 8 and 9 show the inner tubular layer 42 in its compressed or folded condition, folded up and fit into the initial elastic lumen 58 of the outer tubular layer. In the compressed condition, the elastic outer tubular layer 40 urges the first longitudinally extending end 66 under the second longitudinally extending end 68 of the inner tubular layer 42. This positions the thin wall portion 64 between the first and second longitudinally extending ends 66, 68.

Figure 10:
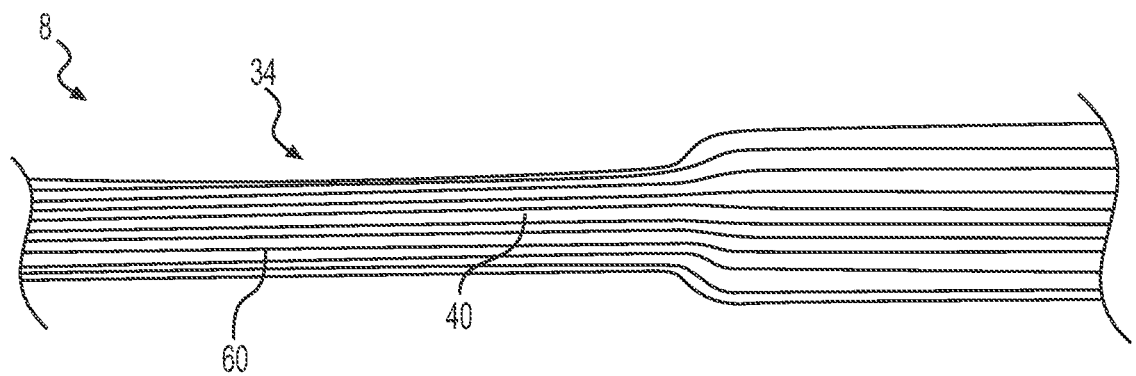
FIG. 10 is a side view of one implementation of the expandable sheath.

FIG. 10 shows a side view of an implant moving through sheath 8. During passage of an implant through the central lumen 38, the tubular wall structure 34 takes on a locally expanded condition corresponding to the length and geometry of the implant 12. In the expanded condition, the first and second longitudinally extending ends 66, 68 radially expand apart, against the urging of the elastic outer tubular layer 40 by passage of the implant 12, into a non-overlapping condition with the thin wall portion 64 extending therebetween to form the expanded lumen, as in FIG. 7. After passage of the implant 12, the inner tubular layer 42 is urged by the outer elastic tubular layer 40 into the compressed condition shown in FIGS. 8 and 9. With this configuration, a 14 French sheath 8 allows passage of a 29 mm transcatheter heart valve, such as the Sapien XT and Sapien 3 transcatheter heart valves available from Edwards Lifesciences.

As another option, the inner tubular layer 42 may be adhered along one or more longitudinally extending portions of the outer tubular layer 40. Adhesion may be by heat fusion between the two layers or adhesive bonding, for example. As shown in FIG. 9, the longitudinally extending portion can be a strip 70 where the outer surface of the inner tubular layer 42 is bonded or otherwise adhered to the inner surface of the outer tubular layer 40. Preferably, the strip 70 is positioned opposite the thin wall portion 64 to be away from, and not affect, the fold of the inner tubular layer 42. Inhibiting folding would also raise the push force for passage of the implant 12. Another implementation may include a second thin bonding strip 70 or line. Although the thickness of the strip 70 can vary, preferably it is relatively narrow to reduce its inhibition of expansion of the two layers and any increases in pushing force. Use of a narrow bonding line between the layers 40, 42 prevents free rotation of the layers with respect to each other while minimizing the effect on push force.

Figure 11:
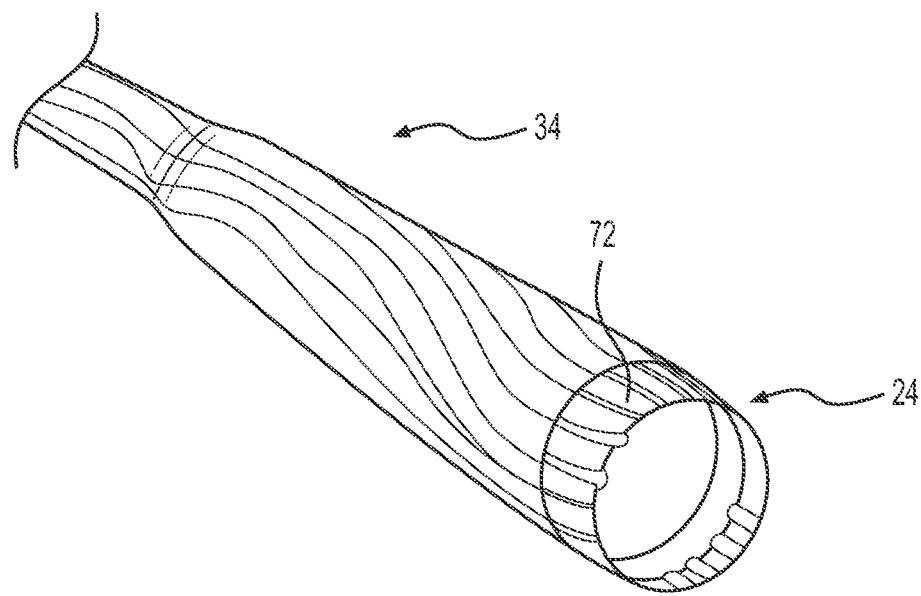
FIG. 11 is a perspective view of one embodiment of a flared distal portion of the sheath.
Figure 14:
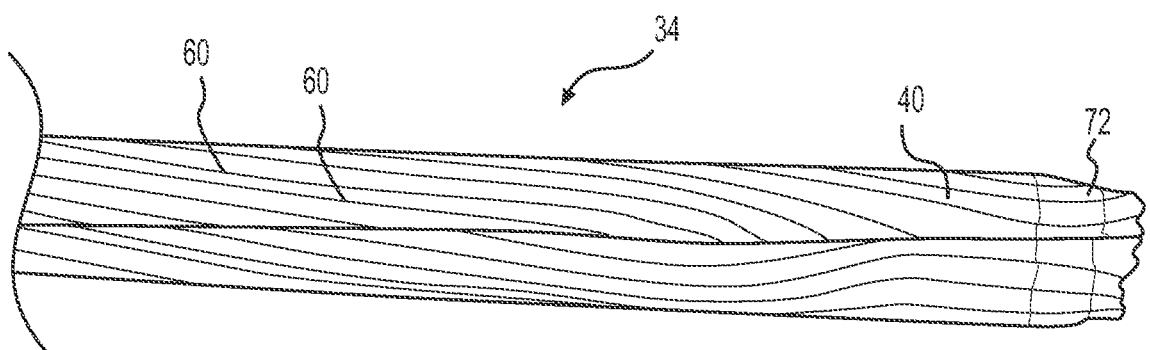
FIG. 14 shows an example flared distal portion of a sheath in a folded configuration.
Figure 15:
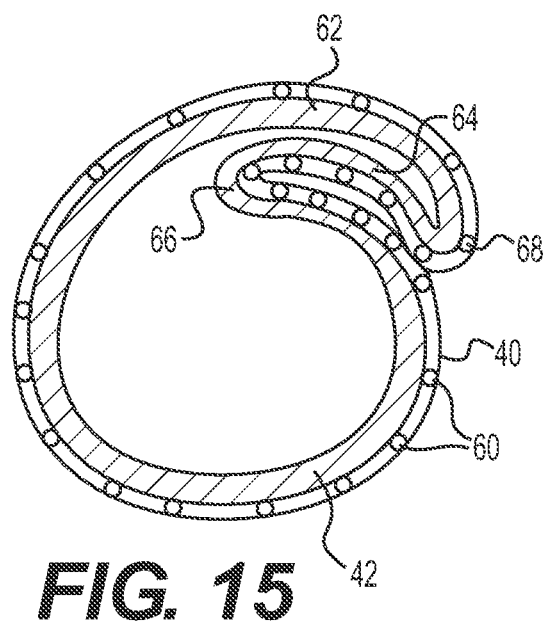
FIG. 15 shows a cross section of a distal portion of a sheath in a folded configuration.
Figure 16:
FIG. 16 shows a sheath during passage of an implant. The inner and outer tubular layers are adhered together in a longitudinally extending strip.

In another embodiment, as shown in FIGS. 11-15, the distal tip 24 of sheath tubular wall structure 34 can be a sealed tip to mitigate blood intrusion and/or facilitate expansion at the distal end of travel of the implant 12. In one aspect, a distal portion of the tubular wall structure 34 may be reflowed to adhere the inner and outer layers 40, 42, as shown in FIG. 11. In particular, the two layers 40, 42 are urged into their fully expanded (unfolded condition) and then reflowed to bind the outer surface of the inner tubular layer 42 to the inner surface of the outer tubular layer 40. Then, the reflowed portion is returned to the compressed or folded configuration and compressed under a heat shrink layer 74 to set the fold. The heat shrink layer 74 is then removed. Thus, when the distal end of the wall structure 34 folds, the outer tubular layer 40 is also folded, as shown in FIGS. 14 and 15. Sealing the tip stops blood from getting between the two layers 40, 42 at the distal end of the sheath 8 while maintaining the highly expandable performance of the tubular wall structure 34.

Figure 12:
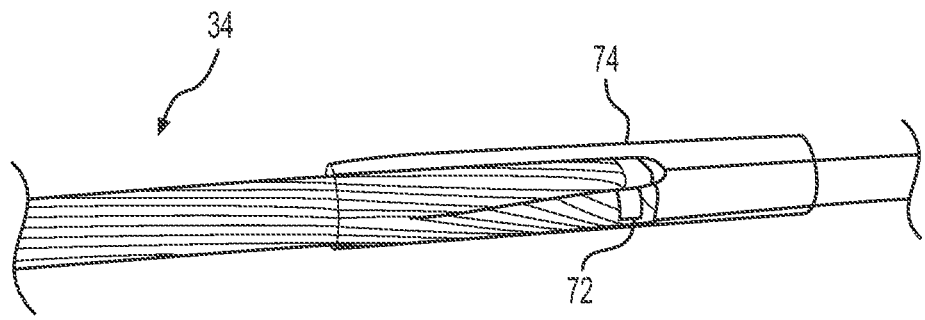
FIG. 12 shows a side view of the distal portion of a sheath folded in a heat-shrink tube.
Figure 13:
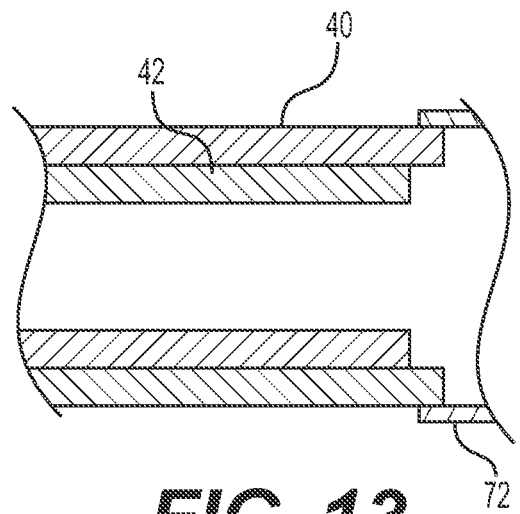
FIG. 13 shows a longitudinal cross section of an embodiment of the distal portion of the sheath including a radioopaque tubular layer.

The reflowed outer tubular layer 40 may have added thereto a radiopaque ring 72. The radiopaque ring 72 can be adhered outside (such as by heat shrinking) and around the reflowed, folded distal portion of the outer tubular layer 40. The ring 72 may be applied (such as by reflowing) outside the outer tubular layer 40 (FIG. 13) or inside the outer tubular layer 40 (FIG. 12). The ring 72 is preferably constructed of a highly elastic polymer to allow expansion and facilitate urging the tip back into a folded configuration.

Advantageously, the outer tubular layer 40 and inner tubular layer 42 are both seamless, which stops blood leakage into the sheath 8. The seamless construction of the inner tubular layer 42 eliminates the ends of a conventional C-sheath. Elimination of the cut in the C-sheath by addition of thin portion 64 improves torque performance. Also, both layers are easily manufactured by an extrusion process. The elastic outer tubular layer 40 has an elastic material that is similar to or the same as most soft tips, making their attachment much easier.

Figure 17:
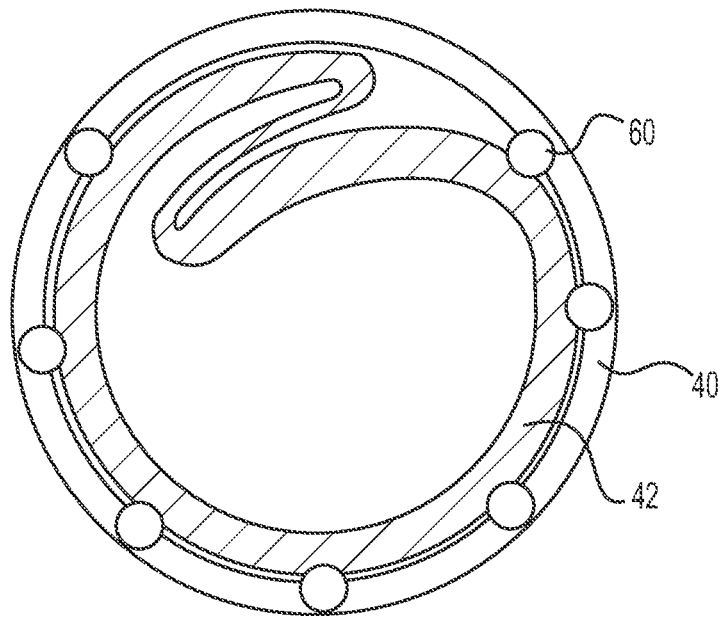
FIG. 17 shows a cross section of an exemplary embodiment including longitudinal rods embedded in the outer tubular layer and protruding into the elastic lumen.
Figure 18:
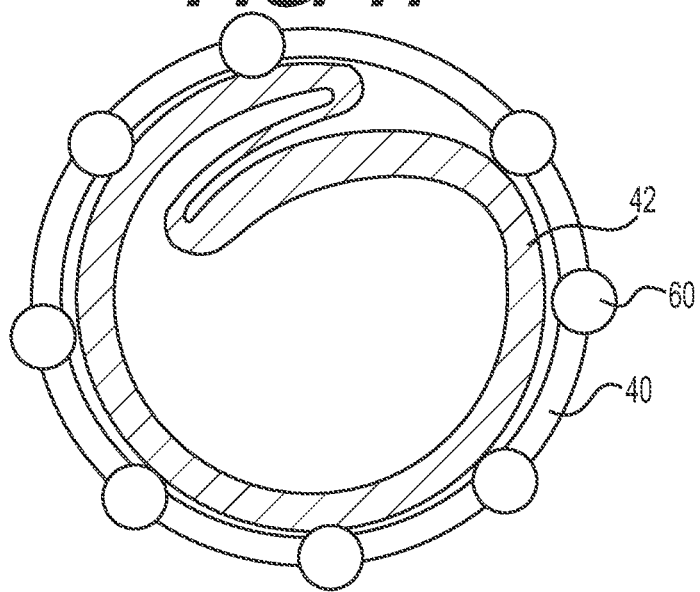
FIG. 18 shows a cross section of an exemplary embodiment including longitudinal rods embedded in the outer tubular layer and protruding into the elastic lumen and outward from the outer surface of the outer tubular layer.

As shown in FIGS. 17-20, other embodiments of the sheath 8 may include a conventional C-shaped inner tubular layer 42 surrounded by an elastic outer tubular layer 40 employing longitudinal rods 60. (FIGS. 17-20 may also use other types of inner tubular layer 42, such as the integrally formed ones disclosed herein.) FIG. 17 shows use of seven longitudinal rods equally spaced from each other about the interior surface of the outer tubular layer 40 with the exception that a rod is missing from a portion adjacent a split in the inner tubular layer 42. This gap facilitates distraction and return of the free edges of the C-shaped inner tubular layer 42. FIG. 18 shows a similar arrangement but with the eighth longitudinal rod 60 present. But the rod is somewhat offset from the location of the free edges of the inner tubular layer 42. Furthermore, the rods of FIG. 18 protrude outward from the outer surface of the outer tubular layer 40 to lower friction between the sheath and, for example, a body lumen or an additional outer delivery sheath.

Figure 19:
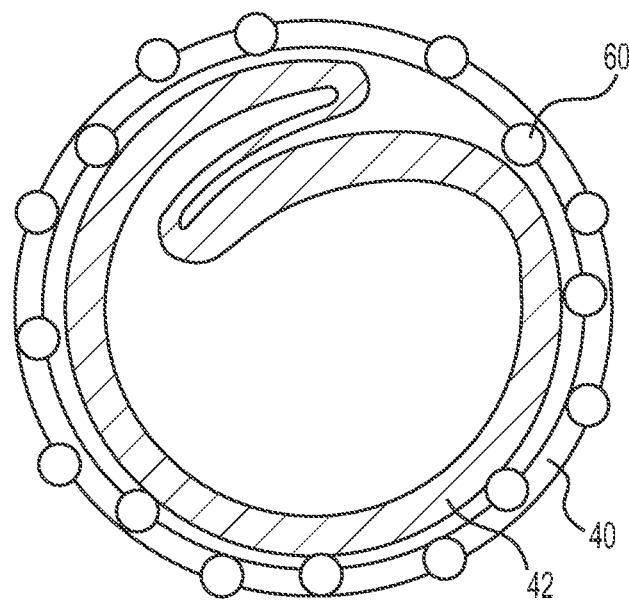
FIG. 19 shows a cross section of an exemplary embodiment including longitudinal rods embedded in the outer tubular layer, where some rods protrude into the elastic lumen and others protrude outward from the outer surface of the outer tubular layer.
Figure 20:
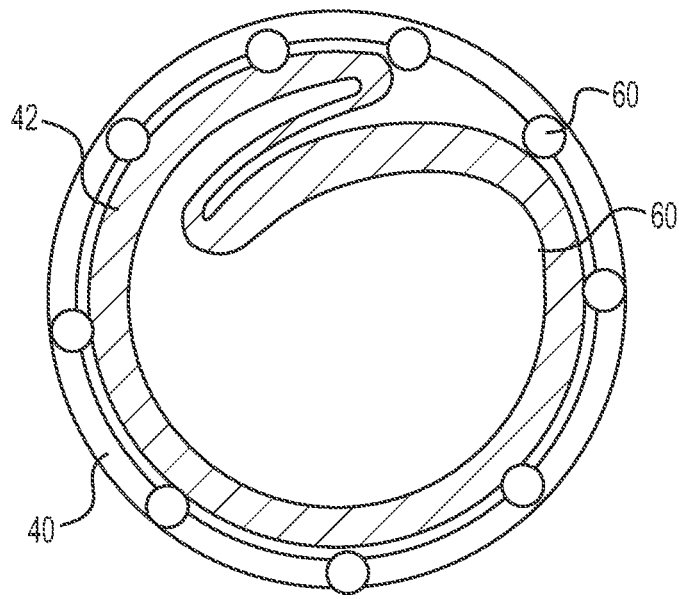
FIG. 20 shows a cross section of an exemplary embodiment including longitudinal rods embedded in the outer tubular layer and the inner tubular layer. The longitudinal rods embedded in the outer tubular layer protrude into the elastic lumen and the longitudinal rods embedded in the inner tubular layer protrude into the central lumen.

FIG. 19 shows another embodiment wherein rods are embedded in the outer tubular layer 40 and extend from the inside and outside surfaces thereof in alternation. This can lower friction from advancement of the sheath 8 wherein, for example, the outer surface of the layer 40 touches a body lumen or additional outer delivery sheath. FIG. 20 shows another embodiment wherein the inner tubular layer 42 also includes a plurality of longitudinal rods 60 that facilitate, for example, easy passage of the implant 12.

The outer tubular layer 40 in the configurations of FIGS. 17-20 still can have a highly elastic, thin structure to fit over the conventional C-sheath inner tubular layer 42. As the outer tubular layer 40 is not adhered to the inner tubular layer 42, there is free movement between the sleeve and the delivery catheter 10. The outer tubular layer 40 is also seamless to guard against blood leakage. The sheath 8 is stretched evenly along all segments in a radial direction—reducing the risk of tearing or fracture. And, the elastic outer tubular layer 40 will urge the C-shaped sheath back into the reduced profile configuration. During construction, the inner layer 42 is easily fitted inside the outer layer 40 without flattening or heat wrapping. Implementations may include a large number of longitudinal rods 60—even 100 or more depending upon their cross-sectional size. The longitudinal rods 60 may include microstructure patterns that further reduce friction.

Figure 21:
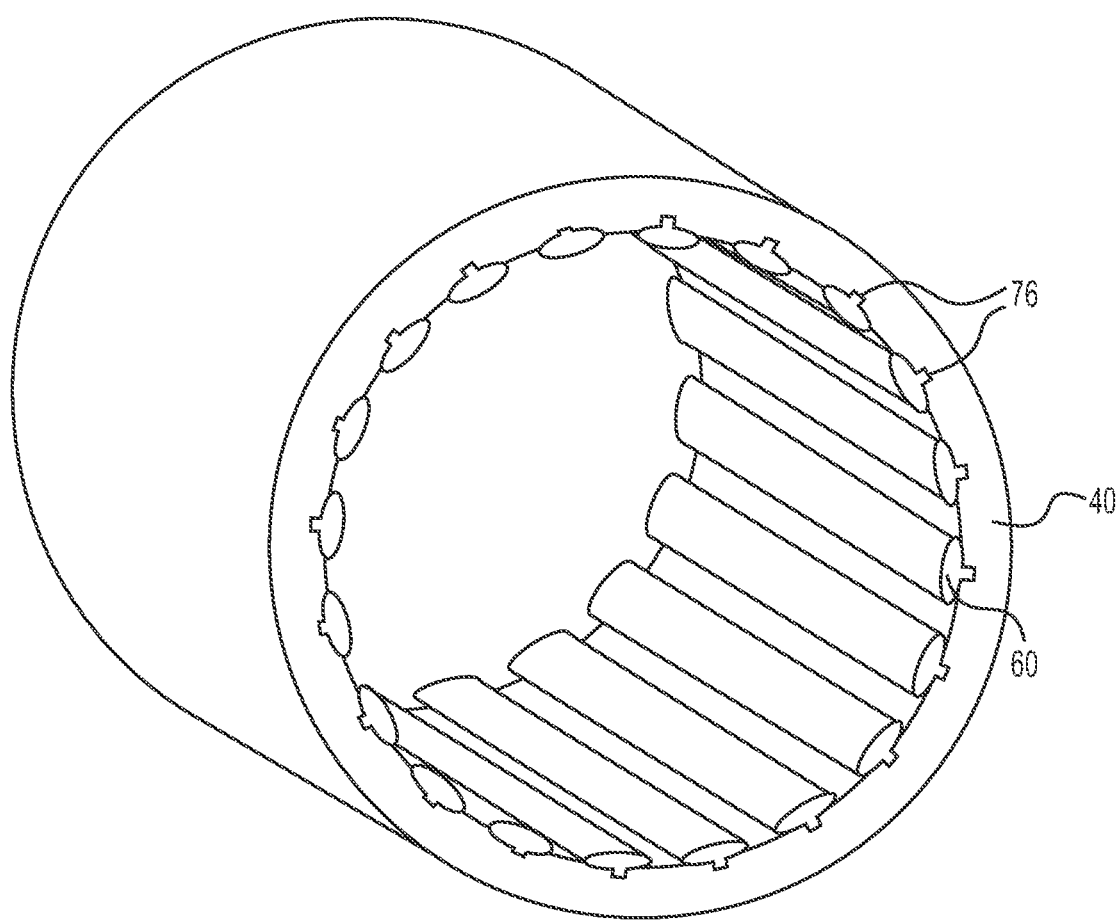
FIG. 21 shows a cross section of another exemplary embodiment including longitudinal rods embedded in the outer tubular layer and protruding into the elastic lumen.
Figure 22:
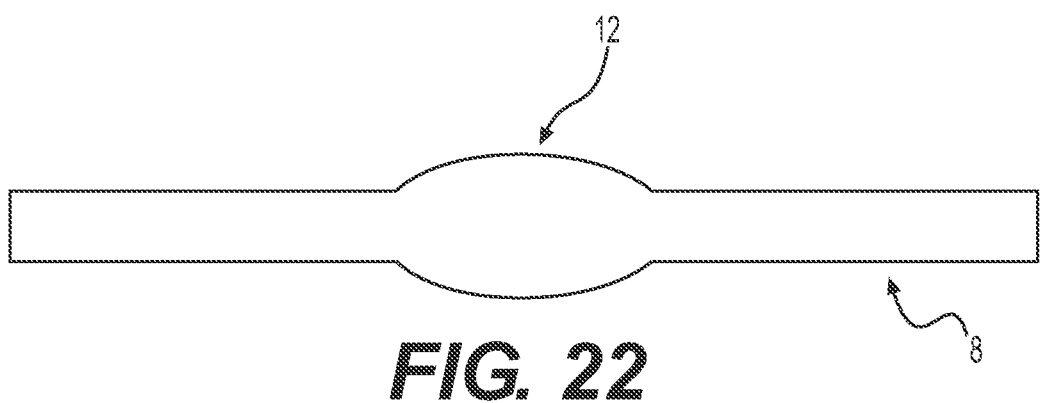
FIG. 22 shows a side view of the sheath with an implant passing therethrough.

FIGS. 21 and 22 show yet another embodiment of the sheath 8 including a segmented outer tubular layer 40 having longitudinal rods 60 that may be employed with or without an inner tubular layer 42. As shown in FIG. 21, the outer tubular layer 40 has elongate cuts or grooves that form elongate segments 76 extending axially along inner surface. Formed or mounted along the grooves are the longitudinal rods 60. The longitudinal rods 60 are shown in FIG. 21 to have curved or arc-shaped top surfaces that reduce friction for passing implants 12. The longitudinal rods 60 are comprised of relatively high stiffness materials such as HDPE, fluropolymer and PTFE. The outer tubular layer 40 can be constructed of highly elastic materials with a low tensile set (TPE, SBR, silicone, etc.) to facilitate recovery after expansion. When used without an inner tubular layer 42, the outer tubular layer 40 can have additionally lowered expansion force—especially because the higher strength material (the rods) are not connected in the radial direction. Other variations may include changing the number and shape of the rods 60, incorporation of a tie layer or undercut/bard to strengthen the connection of the rods to the outer layer 40 and adding sections of stiff material to the outside of the outer layer for improved stiffness and pushability. A slip additive may be applied to the surfaces to increase lubricity. FIG. 22 shows the bulge in the sheath 8 as the implant 12 passes therethrough.

Figure 23:
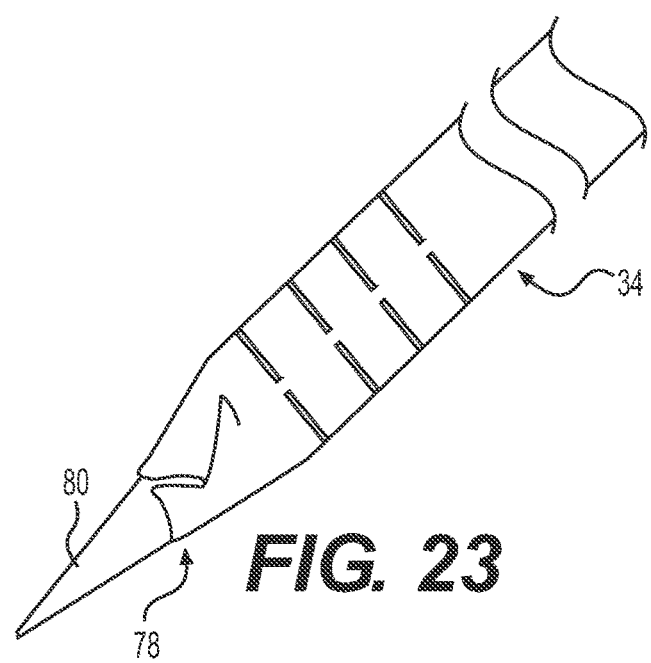
FIG. 23 shows a flared implementation of a distal portion of the sheath, where the flared portion is folded into a compressed configuration.
Figure 24:
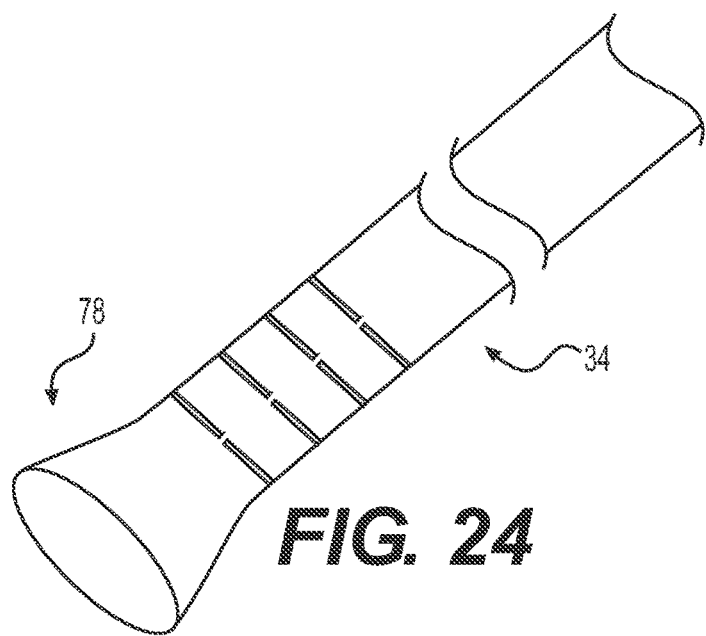
FIG. 24 shows the distal portion of FIG. 23 with the flared portion unfolded and expanded.
Figure 25:
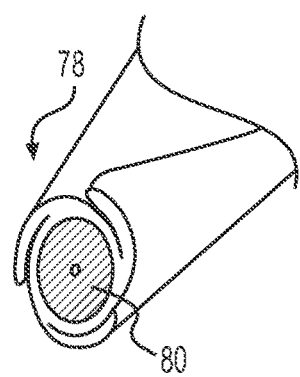
FIG. 25 shows a cross section of the distal portion of FIG. 23, where the flared portion is folded into a compressed condition.

FIGS. 23-25 show another embodiment wherein a distal end of the tubular wall structure 34 can have a flared portion 78. The flared shape of the flared portion 78 helps to reduce snags or interference during retrieval experienced with conventional sheaths during retrieval of medical devices. The flared portion 78 is folded or wrapped around the tapered distal end of an introducer 80 to maintain a low profile for advancement, as shown in FIGS. 23 and 25. The number and size of the folds may vary depending upon the size and material type of the tubular wall structure 34. For example, FIG. 25 shows three folds in a cross-sectional view. After the distal end of the sheath 8 is in position, the introducer 80 is removed. Then, the sheath 8 is ready to receive the delivery catheter 10 and implant 12. When the implant 12 reaches the flared portion 78 the folds then break and expand into the flared configuration, as shown in FIG. 24. The flared portion 78 remains in this flared configuration for possible retrieval of the implant 12.

Figure 28:
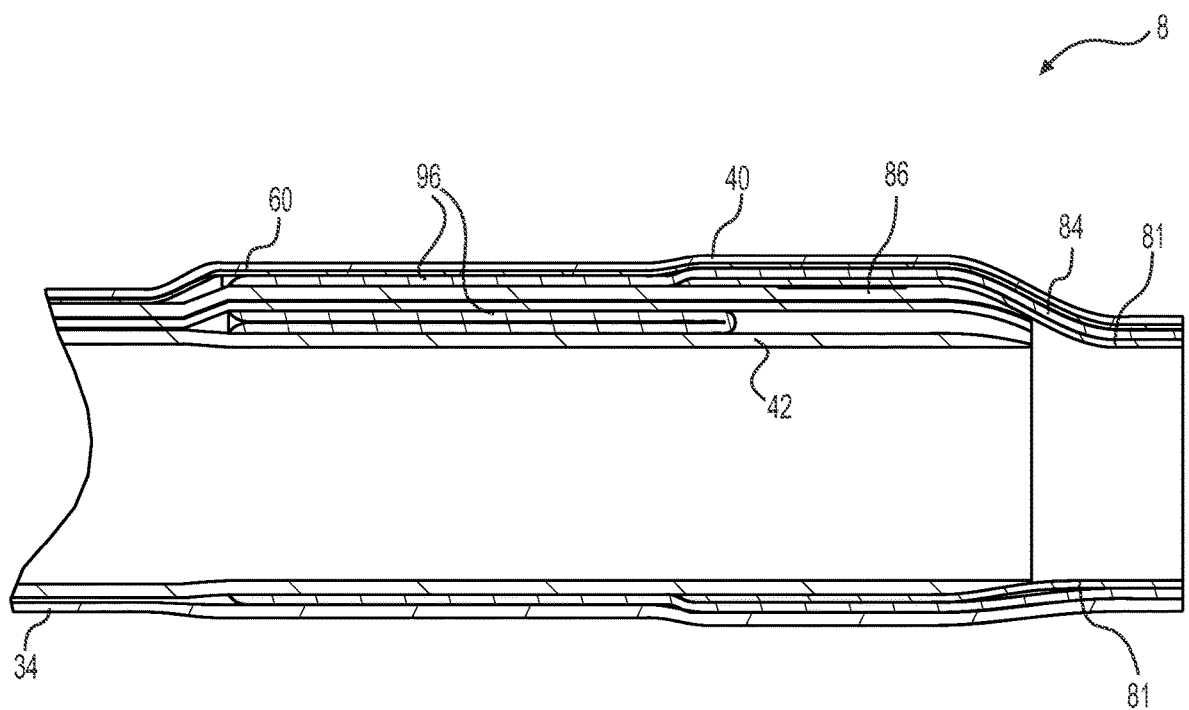
FIG. 28 shows a longitudinal cross section of the distal region of the implementation shown in FIG. 26.
Figure 29:
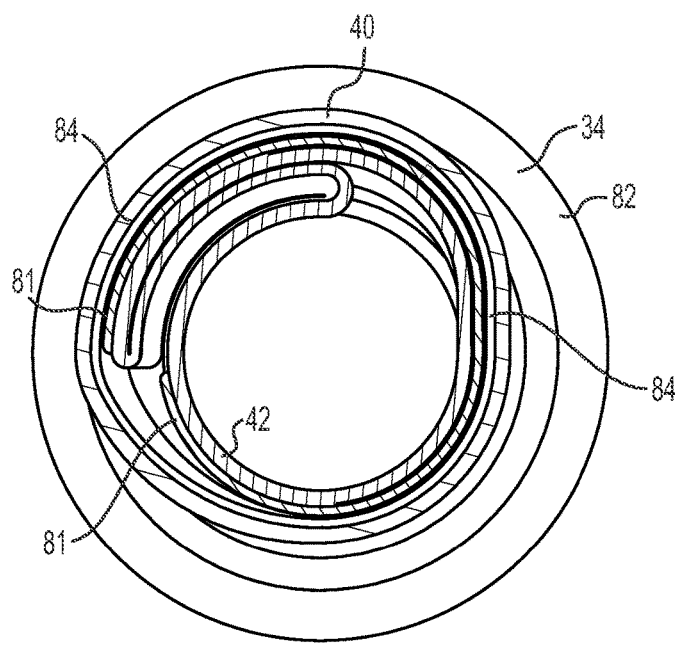
FIG. 29 shows a cross section of the distal region of the implementation shown in FIG. 26.

FIGS. 26-29 show another embodiment of the sheath 8. The sheath 8 includes the tubular wall structure 34 that extends from the proximal end (as shown in cross-section in FIG. 27) to the distal end (FIGS. 28 and 29). Generally, the tubular wall structure 34 includes inner tubular layer 42, inner tip layer 81, strain relief tubular layer 82, outer tip layer 84 and the elastic outer tubular layer 40.

Figures 26, 27:
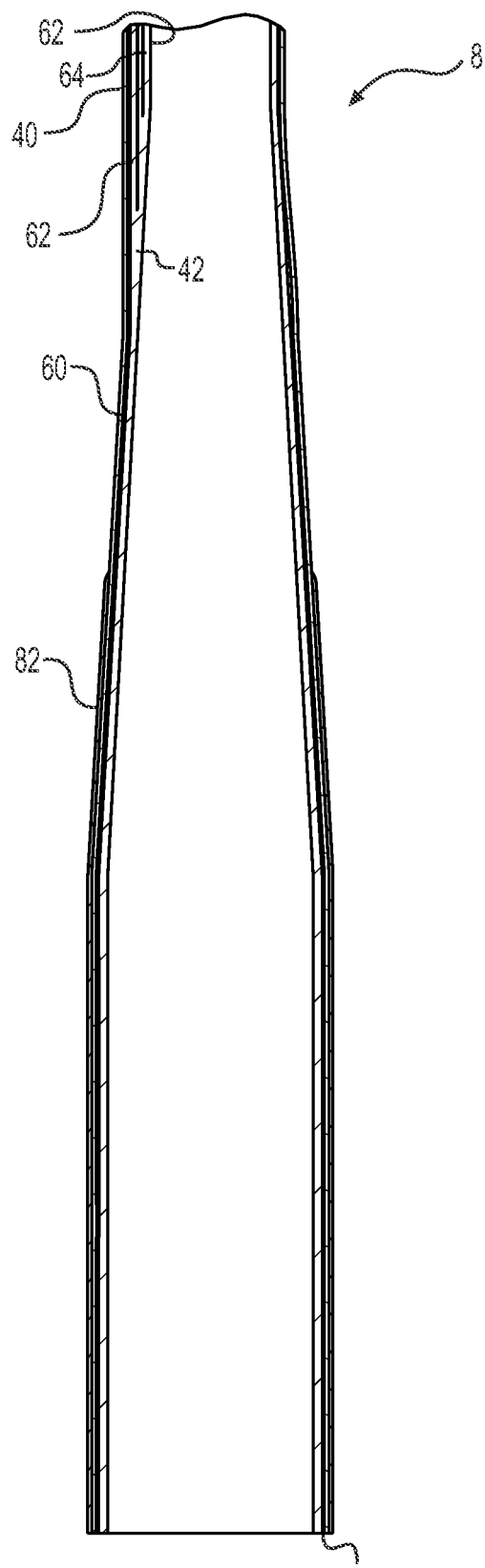
FIG. 26 shows a perspective view of an exemplary implementation of the expandable sheath.
FIG. 27 shows a longitudinal cross section of the proximal region of the implementation shown in FIG. 26.

As can be seen the tubular wall structure 34 has different layers depending up on the axial position. The wall structure 34 includes a strain relief tubular layer 82 that terminates about ⅔ of the way from the proximal end, as shown in FIG. 27. The strain relief layer 82 is preferable comprised of a relatively stiff material, such as HDPE, that can withstand the strains of the proximal end of the sheath 8 where it is joined to the hub and 20 and other components for accepting initial insertion of the delivery apparatus 10. It terminates short of the distal end of the sheath 8 to facilitate a greater flexibility and lower profile of the distal end of the sheath 8.

Extending past the strain relief tubular layer 82 the tubular wall structure 34 drops down to two layers, the inner tubular layer 42 and elastic outer tubular layer 40. On the proximal-most end of the portion of the sheath 8 shown in FIG. 27, the inner tubular layer splits (in cross-section) into its thick wall portion 62 and thin wall portion 64 in the folded over configuration.

At the distal end, as shown in FIGS. 28 and 29, the sheath 8 includes tip structure (including inner tip layer 81 an outer tip layer 84) configured to taper the wall structure 34 and seal the free end of the layers against blood or fluid invasion. Generally, these components build up the diameter of a length of the wall structure 34 with some additional layers including stiffening layers, and then tapers out and over the distal free end of the inner tubular layer 42.

The inner tubular layer 42 is similar to that described above. It includes the thin wall portion 64 that is configured to fold over into the folded configuration back onto the thick wall portion 62. Also, the elastic outer tubular layer 40 restrains the inner tubular layer 42 against expansion. But, the elasticity of the outer tubular layer 40 can also be overcome to allow the inner tubular layer to at least partially unfold into a wider central lumen 38 for passage of the implant 12 or other device.

As shown in FIG. 28, the inner tip layer 81 extends only a short axial length. In particular, the inner tip layer 81 extends around and past the distal-most end of the foldable inner tubular layer 42, tapering into smaller diameter free end after extending distally past the free end of the foldable inner tubular layer. As shown in the cross-section orthogonal to the long axis of the sheath 8 of FIG. 29, the inner tip layer 81 has a C-shaped cross-section. (The top of the C-shape is enlarged somewhat to account for the overlapping layers of the wall structure 34—so that the free longitudinal edges are radially spaced apart to form a gap.) The C-shaped cross-section allows the free longitudinal edges of the inner tip layer 81 to spread apart during unfolding of the inner tubular layer 42. Advantageously, the inner tubular layer 42 has a relatively stiff material construction smoothing, stiffening and tapering the distal end of the sheath 8 as well as providing some protection for the free end of the inner tubular layer 42. The inner tip layer 81 also advantageously extends over the distal end of the inner tubular layer 42, thereby sealing the thick and thin wall portions 62, 64 against blood and fluid invasion.

The outer tip layer 84 extends over and is adhered to the inner tip layer 81 and a distal portion of the inner tubular layer 42. The outer tip layer 84 covers the proximal edge of the inner tip layer 81, sealing it against the inner tubular layer 42. The outer tip layer 84 is of a relatively bendable material and, where it is directly adhered to the thin wall portion 64, can be folded over onto itself as shown in FIG. 28. Advantageously, then, the outer tip layer 84 tracks the unfolding of the thick and thin wall portions 62, 64 to continue to seal the inner tip 81 to the inner tubular layer 42. Notably, as the outer tip layer 84 unfolds the free longitudinal edges of the C-shaped inner tip layer 81 can come apart for coordinated lumen expansion of the sheath 8. But, also, at the same time the stiffness of the inner tip layer 81 and extra reinforcement of the outer tip layer 84 help to maintain tip stiffness and stability.

The elastic outer tubular layer 40 extends all the way to the distal end of the sheath 8, including over the distal end of the outer tip layer 84. In addition, the inside of the elastic outer tubular layer includes rods 60 extending axially and reducing unfolding resistance by lowering surface area and increasing lubricity.

The sheath 8 may also include a radiopaque marker band or layer portion 86 that provides an orientation and depth indication under radioscopy during implantation or other medical procedures.

Figure 30:
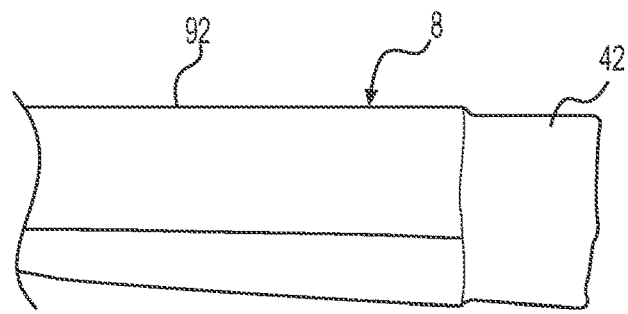
FIGS. 30 through 38 show a method of assembling a stiffened and sealed tip for another embodiment of the expandable sheath.
Figure 31:
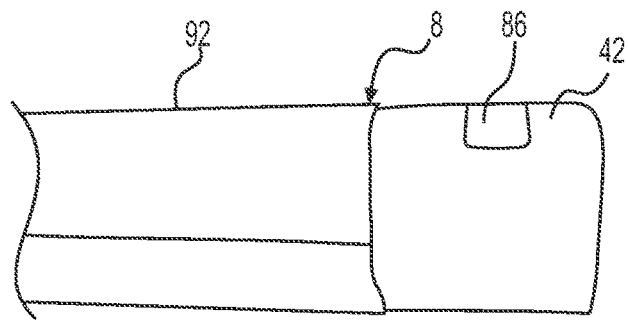

FIGS. 30 through 38 show a method of assembling a stiffened and sealed tip for another embodiment of the sheath 8. FIGS. 30-38 show varying views of the same sheath 8 as it undergoes the method of assembly. FIGS. 30 and 31 show the inner tubular layer 42 (to the right) in the unfolded configuration. An additional tubular layer 92 (such as a strain relief or elastic layer) (to the left) extends over the inner tubular layer 42 but stops short of the free end of the inner tubular layer. FIG. 31 shows a portion of the radiopaque marker 86 attached to the inner tubular layer 42.

Figure 32:
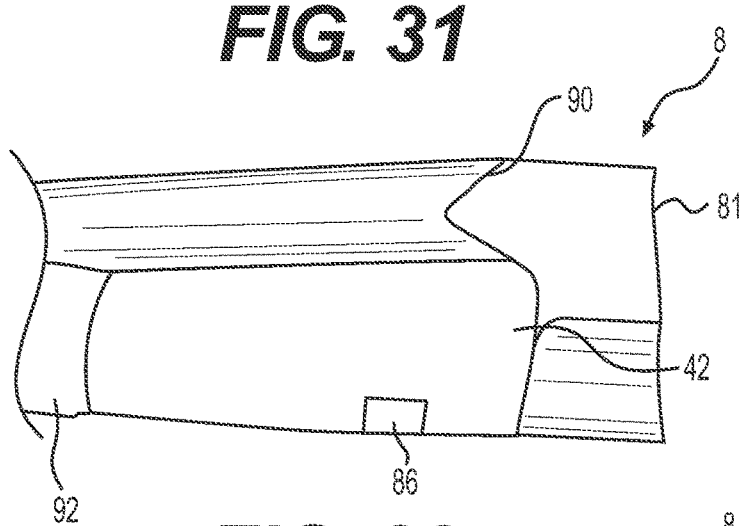
Figure 33:
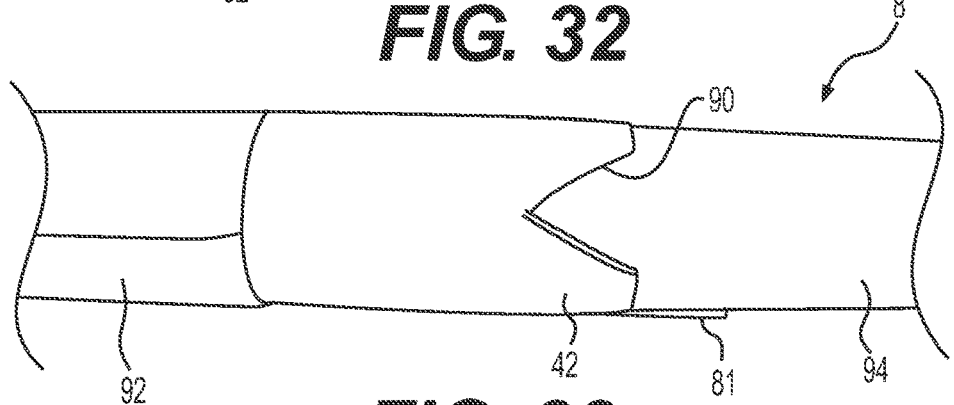

FIG. 32 shows the inner tubular layer 42 with a window or v-shaped notch 90 cut into its free end to allow for tip expansion. The v-shaped notch 90 also facilitates retrieval of an implant. FIG. 32 also shows the C-shaped inner tip layer 81 extended around an outside of the inner tubular layer. FIG. 33 shows a second notch 90 on the opposite side of the inner tubular layer 42. Also in FIG. 33, the distal tip of the partially constructed sheath 8 is extended over a mandrel 94 to facilitate folding and attachment of other layers.

Figure 34:
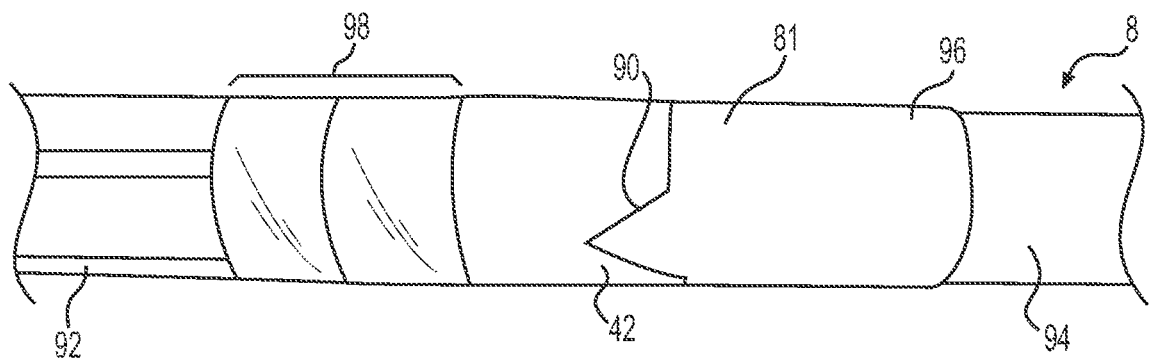

FIG. 34 shows formation of a proximal hemostasis seal by application of a proximal sealing layer 96 that extends around a distal free end of the additional tubular layer 92 and over and past the distal end of the emerging inner tubular layer 42. In the embodiment shown in FIG. 34, the proximal sealing layer 96 is transparent such that the v-shaped notch 90 is visible from underneath the sealing layer 96. A proximal section 98 of the sealing layer 96 is heat treated to seal the transition between the additional tubular layer 92 and the inner tubular layer 42, which in some embodiments can give proximal section 98 a glossier appearance than the remainder of sealing layer 96. The proximal section 98 blocks blood and other fluids from entering between the two layers 42, 92.

Figure 35:
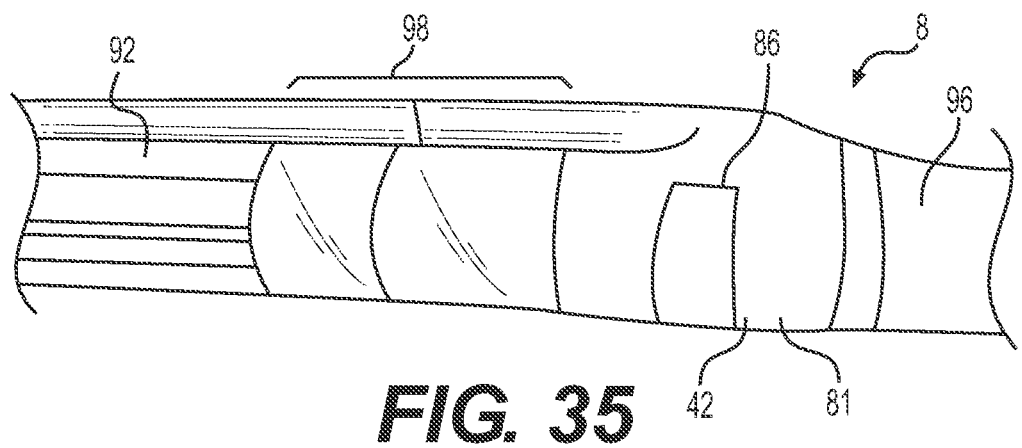
Figure 36:
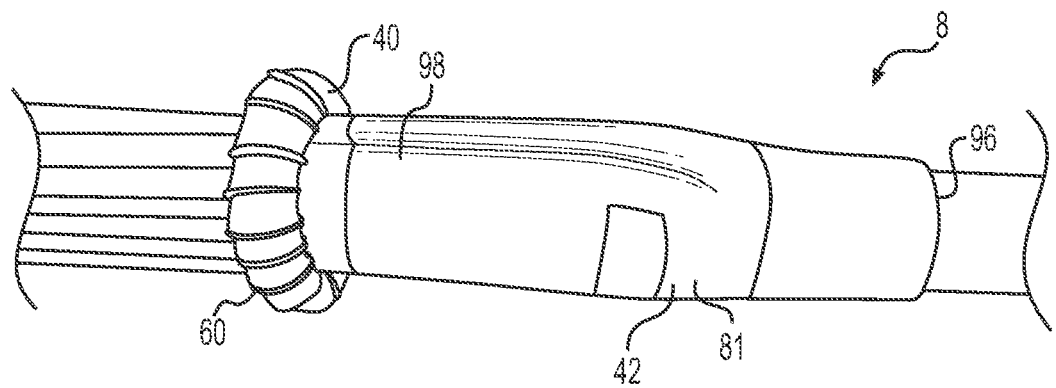
Figure 37:
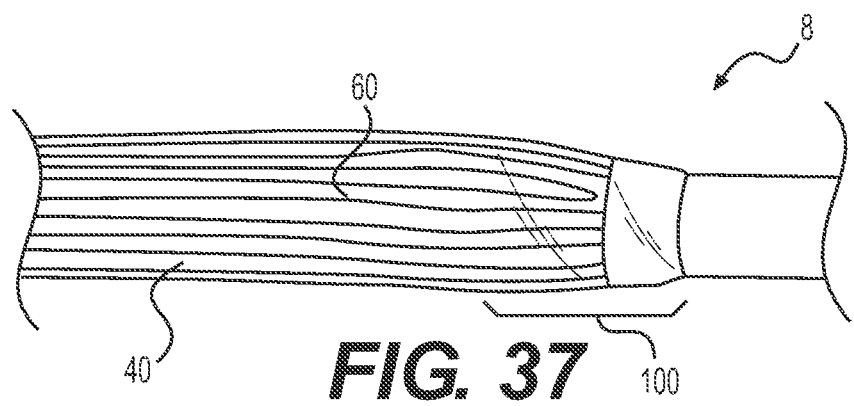
Figure 38:
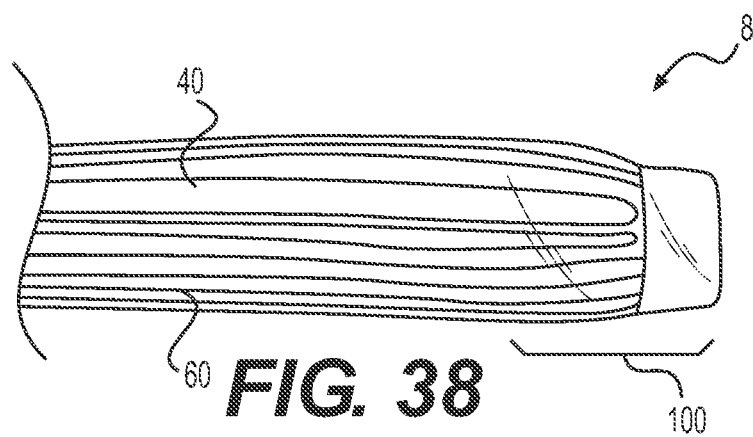

FIG. 35 shows the layers 42, 92 and 96 being folded over onto themselves. FIG. 36 shows the elastic outer tubular layer 40 or jacket with rods 60 being unrolled over the now folded layers 42, 92 and 96. FIG. 37 shows the outer tubular layer 40 itself slightly folded at the distal end and having applied thereover a distal sealing layer 100. The excess of the free end of the proximal sealing layer 96 extending past the distal sealing layer 100 is cut away. The distal sealing layer advantageously urges the distal free end of the layers 40, 42 and 96 into a tapered configuration and provides a rounded distal end for the tubular wall structure 34 that facilitates insertion and advancement over the guidewire.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method of manufacturing an expandable sheath, the method comprising:
   forming multiple longitudinally extending folded portions spaced in a circumferential direction around an inner member, each of the folded portions defined by an overlapping portion bounded between two longitudinally-extending fold edges;
   positioning at least two reinforcing members radially outward of the inner member such that each of the reinforcing members is generally equally spaced from a longitudinal axis of the inner member when the sheath is in a non-expanded configuration, at least one of the reinforcing members is spaced in a circumferential direction from the fold edges of each of the longitudinally extending folded portions, each of the at least two reinforcing members in the form of rods that extend longitudinally along a length of the sheath;

positioning an outer member over the at least two reinforcing members and around the inner member;

binding the outer member to the at least two reinforcing members; and cutting at least one notch in a distal end of the inner member.

2. The method of claim 1, wherein forming the longitudinally extending folded portions comprises overlapping a longitudinal section of the inner member along an outer surface of the inner member.

3. The method of claim 2, wherein overlapping a longitudinal section comprises pinching a longitudinal section of the inner member radially outward from the longitudinal axis of the inner member, then folding the longitudinal section such that an inner surface of the longitudinal section contacts the outer surface of the inner member.

4. The method of claim 1, wherein forming the longitudinally extending folded portions comprises overlapping a longitudinal section of the inner member along an inner surface of the inner member.

5. The method of claim 4, wherein overlapping the longitudinal section comprises pinching the longitudinal section of the inner member into a lumen of the inner member, then folding the longitudinal section such that an inner surface of the longitudinal section contacts the inner surface of the inner member.

6. The method of claim 1, wherein forming the longitudinally extending folded portions comprises arranging two or more longitudinally extending segments of the inner member into an overlapping configuration to form the folded portions.

7. The method of claim 6, wherein arranging two or more longitudinally extending segments of the inner member into an overlapping configuration to form the longitudinally extending folded portions further comprises wrapping the folded portions along an inner or outer surface of the inner member.

8. The method of claim 6, wherein arranging two or more longitudinally extending segments of the inner member into an overlapping configuration to form the longitudinally extending folded portions comprises pinching first and second longitudinal segments of the inner member, then overlapping the pinched longitudinal segments with an inner surface of the inner member.

9. The method of claim 6, wherein arranging two or more longitudinally extending segments of the inner member into an overlapping configuration to form the longitudinally extending folded portions comprises pinching first and second longitudinal segments of the inner member, then overlapping the pinched longitudinal segments with an outer surface of the inner member.

10. The method of claim 1, further comprising spacing the longitudinally extending folded portions equally in the circumferential direction around the inner member.

11. The method of claim 1, wherein each of the longitudinally extending folded portions is circumferentially bounded by two radially outwardly positioned reinforcing members.

12. The method of claim 2, wherein positioning at least two reinforcing members comprises orienting the at least two reinforcing members generally parallel to each other and to a central longitudinal axis of the sheath, wherein a majority of the overlapping section of the inner member is provided between the at least two reinforcing members.

13. The method of claim 1, wherein binding the outer member over the at least two reinforcing members comprises heating the outer member and the reinforcing members.

14. The method of claim 13, wherein heating the outer member and the reinforcing members causes the reinforcing members to become embedded within a wall of the outer member.

15. The method of claim 1, wherein cutting at least one notch comprises cutting the notch in a v-shape.

16. The method of claim 1, further comprising applying a lubricious coating to an inner surface of the outer member.

17. The method of claim 1, further comprising attaching the expandable sheath to a proximal hub.

18. A method of manufacturing an expandable sheath, the method comprising:

forming a longitudinally extending folded portion on an inner member, the longitudinally extending folded portion comprising a portion of the inner member circumferentially overlapping an other portion of the inner member and bounded between two fold edges;

positioning at least two reinforcing members radially outward of the inner member such that they extend longitudinally along a length of the sheath and such that they are each equally spaced from a longitudinal axis of the inner member, at least one of the at least two reinforcing members is spaced in a circumferential direction from the fold edges of each longitudinally extending folded portion, each of the at least two reinforcing members in the form of rods that extend longitudinally along a length of the sheath;

positioning an outer member over the at least two reinforcing members and around the inner member; heating the outer member and the reinforcing members to cause the reinforcing members to become embedded within a wall of the outer member; and cutting at least one notch in a distal end of the inner member.

* * * * *